US010393685B2

(12) United States Patent
Voiculescu et al.

(10) Patent No.: US 10,393,685 B2
(45) Date of Patent: Aug. 27, 2019

(54) CELL-ON-CHIP STRETCHABLE PLATFORM FOR MAMMALIAN CELLS WITH INTEGRATED IMPEDANCE SPECTROSCPY TECHNIQUE

(71) Applicant: Research Foundation of the City University of New York, New York, NY (US)

(72) Inventors: Ioana Voiculescu, New York, NY (US); Xudong Zhang, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 316 days.

(21) Appl. No.: 15/241,686

(22) Filed: Aug. 19, 2016

(65) Prior Publication Data
US 2017/0052135 A1    Feb. 23, 2017

Related U.S. Application Data

(60) Provisional application No. 62/207,111, filed on Aug. 19, 2015.

(51) Int. Cl.
*G01N 33/543* (2006.01)
*G01N 27/02* (2006.01)
(Continued)

(52) U.S. Cl.
CPC ........... *G01N 27/026* (2013.01); *C12M 23/20* (2013.01); *C12M 25/00* (2013.01); *G01N 33/521* (2013.01);
(Continued)

(58) Field of Classification Search
CPC .. G01N 27/026; G01N 33/521; G01N 33/543; G01N 33/54366; C12M 25/00;
(Continued)

(56) References Cited

U.S. PATENT DOCUMENTS 8,389,862 B2 *   3/2013  Arora ................. H01L 23/4985
                                                      174/254
9,159,635 B2 *  10/2015  Elolampi ............... H01L 23/13
(Continued)

OTHER PUBLICATIONS

Zhang, X. et al.; Cell-On-Chip Stretchable Platform for Mammalian Cells Studies; 18th International Conference on Solid-State Sensors, Actuators and Microsystems Transducers 2015, Jun. 21-25, 2015, Alaska, USA (1 page).
(Continued)

*Primary Examiner* — Michael L Hobbs
(74) *Attorney, Agent, or Firm* — Peter J. Mikesell; Schmeiser, Olsen & Watts, LLP

(57) ABSTRACT

An impedance spectroscopy biosensor is provided that is fabricated on a stretchable substrate. The stretchable substrate is integrated with an impedance biosensor that undergoes cyclic strain without cracking. The biosensor is formed by curing an elastomer precursor while on a pre-tensioned membrane that includes a conductive electrode. The resulting elastomeric material is released from the support after curing which releases the pre-tensioned state to produce the biosensor.

12 Claims, 6 Drawing Sheets

(51) Int. Cl.
*G01N 33/52* (2006.01)
*C12M 1/00* (2006.01)
*C12M 1/12* (2006.01)

(52) U.S. Cl.
CPC ..... *G01N 33/543* (2013.01); *G01N 33/54366* (2013.01); *B01L 2300/0819* (2013.01); *B01L 2300/16* (2013.01)

(58) Field of Classification Search
CPC ............ C12M 23/20; B01L 2300/0819; B01L 2300/16
See application file for complete search history.

(56) References Cited

U.S. PATENT DOCUMENTS

| | | | |
|---|---|---|---|
| 2006/0228723 A1* | 10/2006 | Bradley | B01L 3/50857 435/6.11 |
| 2008/0136052 A1* | 6/2008 | Pelrine | F02G 1/043 264/105 |
| 2011/0169511 A1 | 7/2011 | Nordin et al. | |
| 2016/0052131 A1* | 2/2016 | Lessing | B25J 9/142 361/679.01 |
| 2017/0239821 A1* | 8/2017 | Lessing | B25J 9/142 |
| 2018/0128823 A1* | 5/2018 | Lee | G01N 33/54373 |

OTHER PUBLICATIONS

Zhang, X. et al.; Stretchable Impedance Spectroscopy Sensor for Mammalian Cells Impedance Measurements; Proceedings of the ASME 2014 International Mechanical Engineering Congress & Exposition IMECE2014 Nov. 14-20, 2014, Montreal, Quebec, Canada (4 pages).

Voiculescu, I. et al.; Study of long-term viability of endothelial cells for lab-on-a-chip devices; Sensors and Actuators B: Chemical; Mar. 21, 2013; pp. 696-705; vol. 182; Elsevier.

Liu, L et al.; sensors; A Novel Cell-Based Hybrid Acoustic Wave Biosensor with Impedimetric Sensing Capabilities; Mar. 4, 2013; pp. 3039-3055; 13, MDPI.

* cited by examiner

CELL-ON-CHIP STRETCHABLE PLATFORM FOR MAMMALIAN CELLS WITH INTEGRATED IMPEDANCE SPECTROSCPY TECHNIQUE

CROSS-REFERENCE TO RELATED APPLICATIONS

This application claims priority to and is a non-provisional of U.S. Patent Application 62/207,111 (filed Aug. 19, 2015), the entirety of which is incorporated herein by reference.

BACKGROUND OF THE INVENTION

The subject matter disclosed herein relates to sensors for measuring impedance and more particularly for sensors for measuring impedance caused by biological cells.

The electric cell substrate impedance spectroscopy (ECIS) method was pioneered by Giaever and Keese, and has been extensively studied for over two decades due to its simple structure, easy operation, and sensitive to many cell behaviors and properties. The name "impedance spectroscopy" is derived from the fact that the impedance is generally determined at different frequencies rather than just one. The measurements are generally performed using a small ac electric field over a wide frequency range (100 to 100 kHz). As cells attach on the electrodes, the insulating properties of the cells can be detected, since the cells contribute additional resistance to the circuit. A short time after the cells are seeded on a device, the cells form a monolayer and the impedance values are high. These impedance values will be stable over a period of time, as long as the cells are alive. When cells start to die, the cells lose the dielectric properties and there will be a decrease in the measured membrane impedance. Morphological information about the cells on the electrode surface could be extracted from the recorded impedance readings.

The impedance measurements can be correlated to cell size, attachment, growth, proliferation, stiffness and cell viability. The impedance values increase with increasing cell density and reaches equilibrium when the cells are confluent. Normal cell lines adhere more tightly to a surface in comparison to cancer cells. Apoptotic (dead) cells tend to detach from the sensing electrodes and are characterized by very low impedance values approaching zero. Thus, impedance spectroscopy of cell activity is a versatile and sensitive way to detect the response of the cells to a variety of biologically active agents.

At the moment, the most commonly used method to study the cell attachment and proliferations are via assays. This type of assays can only measure the end-point of cell behavior. End point measurements are tedious when a large number of points are required, as the entire treatment and preparation process has to be repeated for each measurement point. Alternative methods of obtaining impedance measurements of living cells is therefore desirable.

The discussion above is merely provided for general background information and is not intended to be used as an aid in determining the scope of the claimed subject matter.

BRIEF DESCRIPTION OF THE INVENTION SUMMARY

Disclosed in this specification is an impedance spectroscopy biosensor that is fabricated on a stretchable substrate. The stretchable substrate is integrated with an impedance biosensor that undergoes cyclic strain without cracking.

In a first embodiment, a method for forming a stretchable impedance sensor for use in electric cell-substrate impedance spectroscopy (ECIS) is provided. The method comprising steps of: disposing a layer of an uncured elastomer precursor between a pre-tensioned stretchable membrane in a tensioned state and a patterned conductive electrode on a rigid support such that the patterned conductive electrode is partially embedded within the uncured elastomer precursor along a bottom surface and side surfaces of the patterned conductive electrode, wherein the tensioned state stretched the pre-tensioned stretchable membrane by at least 4%; curing the layer of uncured elastomer precursor to produce a first layer of elastomeric material, the curing occurring while the stretchable membrane is in the tensioned state; separating the rigid support from the patterned conductive electrode such that the patterned conductive electrode remains embedded within the first layer of elastomer; and releasing the tensioned state on the pre-tensioned stretchable membrane to produce a released stretchable membrane.

In a second embodiment, a stretchable impedance sensor is provided. The sensor comprises a stretchable membrane layer comprising an elastomeric material; a patterned conductive electrode layer that is partially embedded within the stretchable membrane along a bottom surface and side surfaces of the patterned conductive electrode layer and partially exposed along a top surface of the patterned conductive electrode layer, wherein the patterned conductive electrode layer comprises buckles in a first longitudinal direction and cracks in a second longitudinal direction, the first longitudinal direction and the second longitudinal direction being perpendicular.

This brief description of the invention is intended only to provide a brief overview of subject matter disclosed herein according to one or more illustrative embodiments, and does not serve as a guide to interpreting the claims or to define or lithit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Integrating mechanical stretching and ECIS sensing onto a single platform requires biocompatible, highly flexible and reversible stretchable (elastic) materials for device fabrication. In addition, the interfacial impedance of electrode material to electrolyte should be small to improve the sensitivity of the cells impedance measurement. The disclosed device comprises a stretchable membrane that is reversibly elongated to create cyclic mechanical pulses on cells. Microelectrodes (e.g. microelectrodes fabricated from gold (Au)) on the stretchable membrane are used to record the impedance values of endothelial cell membranes during the differentiation process.

Integrating mechanical stretching and EICS sensing onto a single platform uses reversible stretchable (elastic) materials for device fabrication. The electrode material should be biocompatible, highly flexible, and reversible in the sense that after stretching is finished the material returns to the initial dimensions. In addition, the interfacial impedance fabricated with this material should be small because electrode-electrolyte interfacial impedance is high desirable to the sensitivity of the cells impedance measurement.

Figure 1:
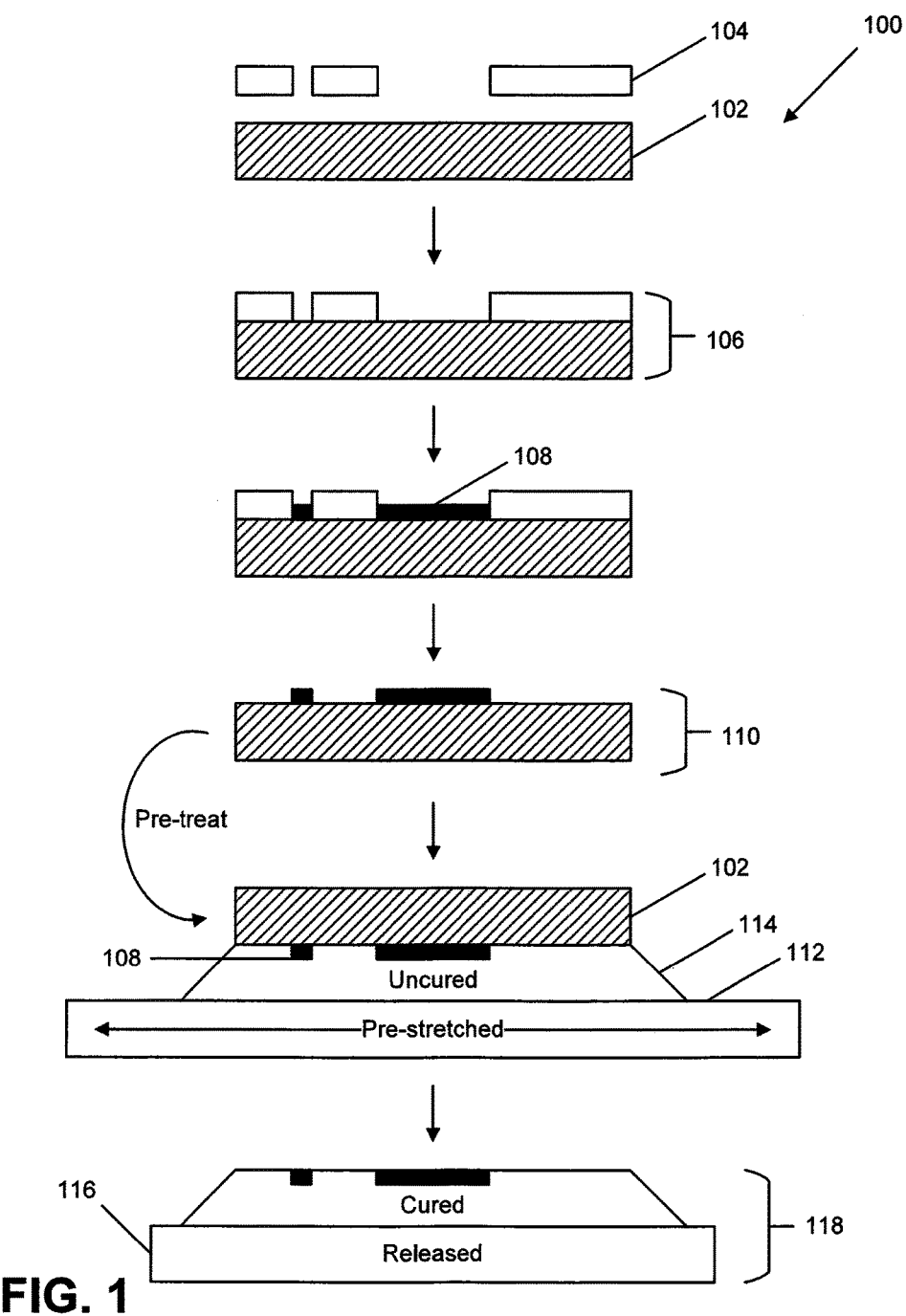
FIG. 1 is a flow diagram of one method for fabricating a stretchable impedance sensor.

An exemplary fabrication method 100 is illustrated in FIG. 1. In one embodiment, a shadow mask 104 is disposed on rigid support 102 (e.g. a glass support, a silicon wafer or rigid plastic polymer) to form an assembly 106. A conductive electrode 108 is formed on the rigid support 102 in a pattern that is predetermined by the shadow mask 104 using conventional masking techniques (e.g. sputtering, chemical vapor deposition, etc.). In one embodiment, the conductive electrodes have a thickness of between 20 nm and 100 nm. In one embodiment the thickness is between 40 nm and 60 nm. The conductive electrode is flexible such that stretching of the resulting sensor does not break the conductive electrode. In one embodiment, the conductive electrode 108 is a layer of conductive material (e.g. gold, platinum, silver powder or carbon nanotubes (CNTs)). Electrode materials used in conventional ECIS sensors are Au and Pt. The shadow mask 104 is subsequently removed to provide an assembly 110. A stretchable membrane 112 of an elastomeric material (e.g. cured PDMS or other silicon based elastomers) is pre-stretched along an axial direction. While the stretchable membrane 112 is in a pre-stretched state (by, for example, application of a stretching force) a layer of uncured elastomeric material 114 is disposed on a top surface of the stretchable membrane 112 and/or on the surface of the assembly 108 that bears the conductive electrode 108. In one embodiment, the pre-stretched state stretches the stretchable membrane 112 by at least 4%. In another embodiment, the pre-stretched state stretches the stretchable membrane 112 by at least 8%. In yet another embodiment, the pre-stretched state stretches the stretchable membrane 112 by at least 10%. In one embodiment, the pre-stretched state stretches the stretchable membrane 112 by less than 20%. In this fashion the uncured elastomeric material 114 is applied as a glue. The assembly 110 is then disposed on the layer of uncured elastomeric material 114 such that the conductive electrodes 108 are at least partially submerged. In one embodiment, the composition of the uncured elastomeric material 114 and the stretchable membrane 112 are the same (e.g. both are PDMS). The uncured elastomeric material 114 is then cured and the rigid support 102 is subsequently removed. During the curing the uncured elastomeric material 114 becomes integrated into the stretchable membrane 112. The stretching force is removed to permit the pre-stretched stretchable membrane 112 to relax to form a released stretchable membrane 116. In this fashion, a stretchable impedance sensor 118 is formed.

In one embodiment, assembly 110 is subjected to a pre-treatment step before the conductive electrodes 108 are at least partially embedded within the uncured elastomeric material 114. This pre-treatment enhances the adhesion of the conductive electrodes 108 to the uncured elastomeric material 114. For example, when the conductive electrodes 108 are gold electrodes, then the pre-treatment may include pre-treatment with a thiol compound such as the thiol compound sold as BT306 (BMT Biosystems, Woodbridge, Conn.). The stretchable impedance sensor provides an integrated ECIS sensor that simulates and replicates the dynamic environment of organism and enables the analysis of the cell activity in vitro.

Figure 2:
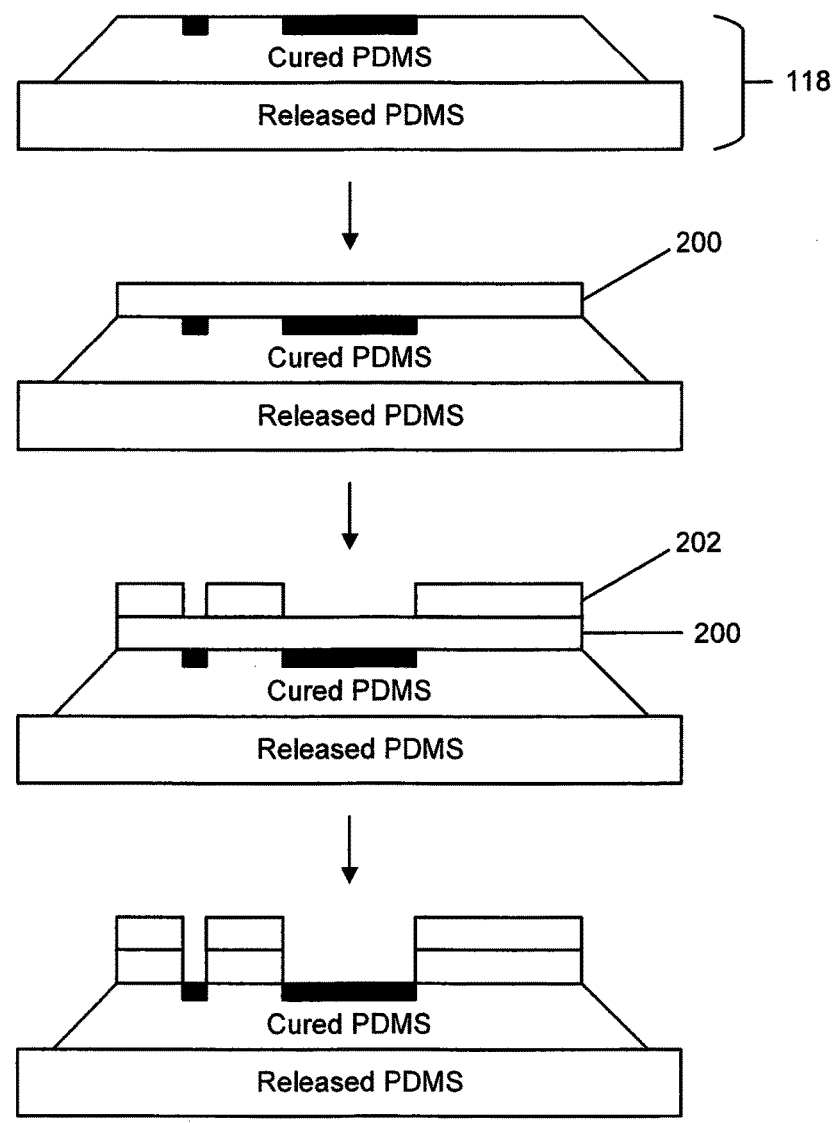
FIG. 2 is flow diagram of another method for fabricating a stretchable impedance sensor.

Referring to FIG. 2, in some embodiments, additional layers are added to the stretchable impedance sensor 118. In the embodiment of FIG. 2, a thin layer of elastomeric material 200 (e.g. a 1-6 micron layer of PDMS) is coated to a top surface of the stretchable impedance sensor 118. A shadow mask 202 is disposed on the layer of elastomeric material 200. Select portions of the thin layer of elastomeric material 200, which are selected according to the predetermined pattern of the shadow mask 202, are selectively removed to provide microgrooves in the elastomeric material 200. Suitable removal techniques include plasma etching techniques such as inductively coupled plasma (ICP) etching.

Figure 3:
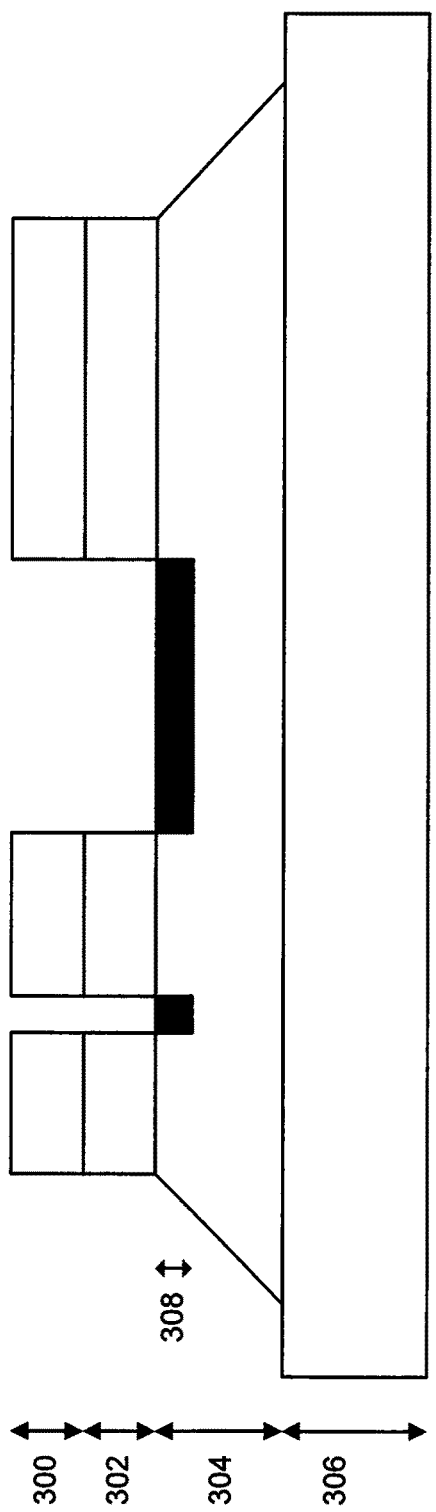
FIG. 3 is a schematic view of one embodiment of a stretchable impedance sensor.

FIG. 3 depicts one embodiment that illustrates thicknesses of various layers. The thickness 300 of the shadow mask 202 is generally between 0.05 mm and 0.25 mm. The thickness 302 of the elastomeric material 200 is generally between 1 micron and 6 microns and, in one embodiment is between 3 microns and 4 microns. The thickness 304 of the cured elastomeric material (from the uncured elastomeric material 114) is generally between 0.3 mm and 0.5 mm. The thickness 306 of the released elastomeric material 116 is generally between 1.5 mm and 2.5 mm. The thickness 308 of the conductive electrode 108 is generally between 20 nm and 100 nm and, in one embodiment is between 40 nm and 60 nm. The entire device is therefore generally between 1 mm and 5 mm thick and, in one embodiment, is between 1.8 mm and 3.3 mm thick.

EXAMPLE

Bovine aortic endothelial cells (BAEC) were cultured on the stretchable membrane and were used to investigate the strain effect on the cells and cells viability using the ECIS technique. Details of the ECIS electrodes fabrication on a stretchable membrane are provided in detail elsewhere in this specification.

The pattern of electrodes were designed with LAYOUT-EDITOR™ software, and fabricate by cutting a thin metal sheet with laser cutter equipment to fabricate the shadow mask. The stretchable membrane was fabricated from PDMS. For this fabrication SYLGARD® 184 silicone elastomer kit (ML SOLAR, Campbell, Calif.) was used, in which the mixing ratio of the monomer and curing agent was 10:1. The PDMS layer was fabricated with a thickness of 2000 µm. The external dimensions of the PDMS membrane were 60 mm×44 mm×2 mm. Sputtering equipment from Hummer XP (Anatech, Union City, Calif.) was used to deposit 50 nm Au on glass slide covered with shadow mask to form conductive electrodes. After taking away the shadow mask, the glass slide was immersed into BT306 (BMT Biosystems, Woodbridge, Conn.) for one hour to improve the bonding ability between Au electrodes and PDMS. BT306 can form strongly bond on the surface of Au electrode and uncured PDMS, which was found to have better performance than chromium because the cracks on Au electrodes will expose the chromium to cell and culture medium if it was used as interlayer to improve the attachment between Au electrode and PDMS. After that, the glass slide with Au electrodes on it, was rinsed by isopropyl alcohol (IPA) to remove residual BT306. Then, the glass slide was glued on the pre-stretched PDMS substrate with an uncured PMDS mixture. The PDMS substrate was maintained in a stretched state until curing was complete. After curing the PDMS mixture, the glass slide was peel off from the PDMS substrate. Uncured PDMS was used to cover the Au wire in the area of ECIS sensor in order to improve the accuracy and stability of ECIS sensor and protect the Au wire from breaking and wrinkling during cyclic stretch and release.

The profile and conductivity of sputtered Au electrode were inspected after applying cyclic strain. Microscopic images showed cracks and buckles in the Au electrodes after releasing from pre-stretch. Due to the difference of young's modulus of PDMS substrate and Au electrodes, buckling and wrinkling appeared in the pre-stretch direction, and cracks were generated in the direction perpendicular to pre-stretch direction. After the PDMS layer was released from the vise, the resistance of buckling Au electrode were measured and it was found that they still have good conductivity.

Figure 4:
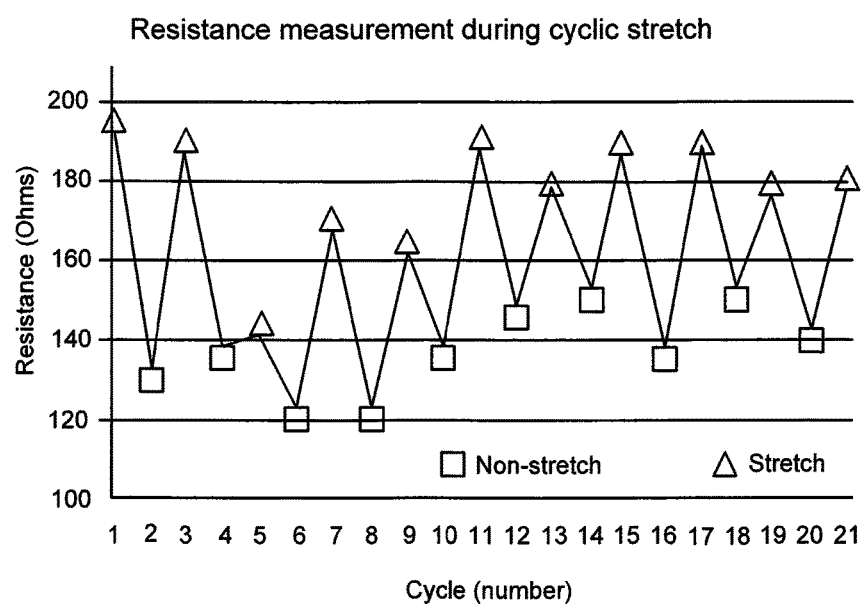
FIG. 4 is graph depicting resistance values for stretched and non-stretched impedance sensors as a function of cycle number.

Resistance measurements were performed to inspect the conductivity of Au electrodes. After the PDMS substrate was released from the vise, the conductivity of Au electrodes was measured using a CASCADE probe station. 20% strain was applied on PDMS membrane with twenty stretching and releasing cycles. The resistance of the gold layer was tested during these cycles. The resultant resistance was illustrated in FIG. 4. The resistance increased when the substrate was stretched and decreased when the substrate was released. The resistance varied during stretching and releasing the PDMS substrate, due to the changes of cross section and length of Au electrodes. As illustrated in FIG. 4, the maximum resistance is 195Ω and the minimum value is 120Ω, the resistance values during first four cycles are not stable, because the Au electrodes start to crack and buckle gradually from the beginning. However after more than four cycles, the resistance variations have more stable trend during stretch and release cycle. Those resistance variations of Au electrode will not influence the sensing ability of impedance spectroscopy of cell morphology during cyclic stretch and release, since the impedance between working and counter electrodes after seeding cell or only introducing cell culture medium was higher enough to ignore those influence.

These results show the stretchable membrane underwent cyclic 20% strain without cracking. The Au electrode attached firmly to the PDMS stretchable membrane, even buckling and cracks appeared, the Au electrodes still do not shed from the substrate. The resistance of Au electrodes varied between 120Ω and 195Ω during cyclic strain, which makes it possible to monitor and analyze the cell activity using ECIS technique, since the impedance value is higher enough to get rid of the influence of resistance variation of Au electrodes. Stretchable membrane integrated with ECIS sensor can simulate and replicate the dynamic environment of organism and enable the analysis of the cell activity in vitro.

Surface modification was performed on the sensor surface, in order to improve the cells attachment. Oxygen plasma treatment was performed on the sensor, then (3-Aminopropyl) triethoxysilane (APTES) was used to modify the treated surface. Then 0.1% gelatin (G2500, Sigma Aldrich) and 30 µg per mL fibronectin (F-1141, GIBCO, Grand Island, N.Y.) were used to form the extracellular matrix (ECM) on the sensor surface.

Figure 5A:
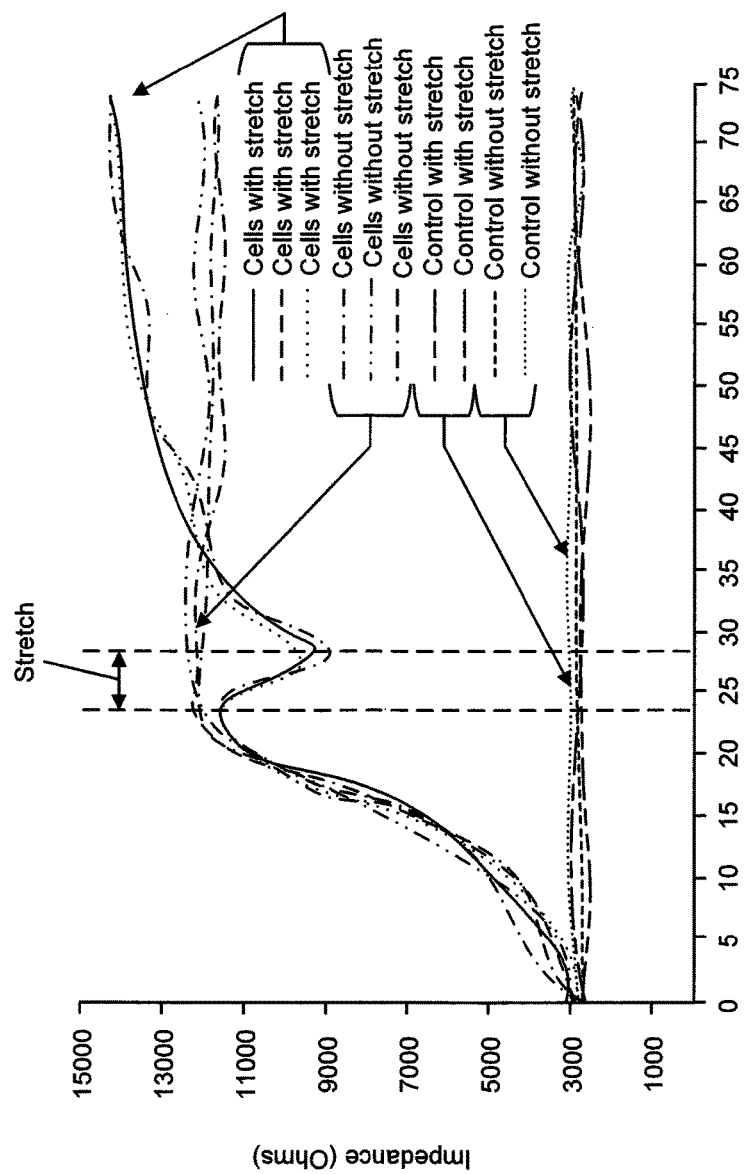
FIG. 5A and FIG. 5B are graphs depicting impedance of stretched and non-stretched samples (FIG. 5A) and normalized impedance comparing the stretched and non-stretched samples (FIG. 5B) values as a function of time for an example of a stretchable impedance sensor.

The cyclic stretch and release were realized by using linear slide system with pitch of 8 mm and travel of 100 mm (Haydon Kerk, Waterbury, Conn.), the stage of linear stage was actuated by a stepping motor with 1.8 degree/step, the motor driver IC was TB6560AHQ. Excitation mode of stepping motor, 4W1-2-phase (16 microsteps) was set to drive the motor. The stage of linear slide can move 0.005 mm per step. LABVIEW® programs were applied to control the motor driver and impedance analyzer Agilent 4294A. The impedance data was acquired at the end of each stretch/release cycle. During this study, BAEC were cultured in Minimum Essential Medium (MEM, GIBCO, Grand Island, N.Y.) with 10% fetal bovine serum (FBS, GIBCO, Grand Island N.Y.). The cell were cultured under standard cell culturing conditions of 37° C. and 5% $CO_2$. BAECs were seeded onto stretchable substrate ECIS sensor, which was pre-coated gelatin and fibronectin on it, with seeding density of 30,000 cells per $cm^2$, according to previous experimental experience. The frequency of impedance analyzer was set to be 7768 Hz and the strain was 10%. FIG. 5A shows the impedance response from ten sensors started when BAECs were seeded on some sensors. The BAECs were cultured on the sensors for 24 hours before stretching to allow the cell attached on the sensor firmly. The frequency of impedance measurement was 9000 Hz and the sensor was stretched by 8% for 4 hours. Then stretching was stopped but the impedance measurements were continuously performed for the next 50 hours. Three sensors seeded with BAECs were stretched 8% for 4 hours. Three sensors seeded with BAECs were not stretched. The control sensors contained only cell culture medium. Two control sensors were stretched by 8% for 4 hours. The rest two control sensors were not stretched.

Figure 5B:
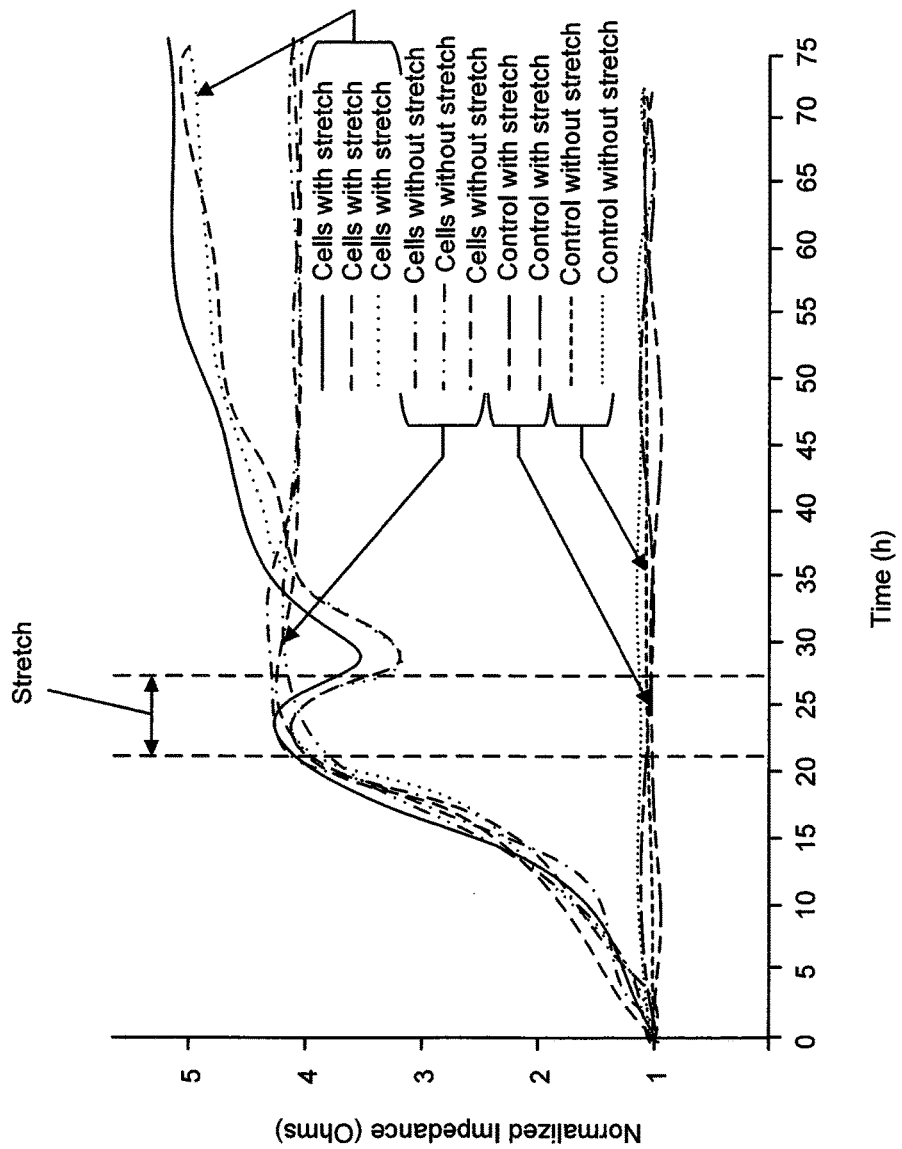

FIG. 5A also shows impedance after BAEC was seeded but not stretched. In both cases Bovine Artery Endothelial Cells (BAECs) were cultured on the device for twenty hours before stretching. Cyclic stretching of 8% with a frequency of 1 Hz was applied on the cells for four hours. The device cyclic elongation was stopped but the impedance measurements were continuously performed for fifty hours. The cell elongation was observed to improve the cells proliferations and, as a result, the corresponding impedance values of the cell membrane exposed to stretching increased. The control contained cell culture medium. FIG. 5B shows the normalized impedance response. The impedance increased gradually, and was stable after the cell form monolayer on the sensor. However, the impedance of control slightly varied due to the influence of resistance variation of Au electrodes.

The impedance measurement was only carried out when the device is not stretched in order to get rid of the resistance variations during stretching.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for forming a stretchable impedance sensor for use in electric cell-substrate impedance spectroscopy (ECIS), the method comprising steps of:
    disposing a layer of an uncured elastomer precursor between a pre-tensioned stretchable membrane in a tensioned state and a patterned conductive electrode on a rigid support such that the patterned conductive electrode is partially embedded within the uncured elastomer precursor along a bottom surface and side surfaces of the patterned conductive electrode, wherein the tensioned state stretched the pre-tensioned stretchable membrane by at least 4%;
    curing the layer of uncured elastomer precursor to produce a first layer of elastomeric material, the curing occurring while the pre-tensioned stretchable membrane is in the tensioned state;
    separating the rigid support from the patterned conductive electrode such that the patterned conductive electrode remains embedded within the first layer of elastomeric material;
    releasing the tensioned state on the pre-tensioned stretchable membrane to produce a released stretchable membrane.

2. The method as recited in claim 1, wherein the patterned conductive electrode has a thickness between 40 nm and 60 nm.

3. The method as recited in claim 1, wherein the layer of the uncured elastomer precursor has a thickness between 0.3 mm and 0.5 mm.

4. The method as recited in claim 1, wherein the tensioned state stretched the pre-tensioned stretchable membrane by at least 8%.

5. The method as recited in claim 1, wherein the tensioned state stretched the pre-tensioned stretchable membrane by at least 10%.

6. The method as recited in claim 1, wherein the patterned conductive electrode consists of gold.

7. The method as recited in claim 1, wherein the uncured elastomer precursor comprises a polydimethylsiloxane precursor such that the first layer of elastomeric material consists of polydimethylsiloxane.

8. The method as recited in claim 1, further comprising coating the patterned conductive electrode with an adhesive prior to the step of disposing.

9. The method as recited in claim 8, wherein the adhesive is a thiol adhesive and the patterned conductive electrode is gold.

10. A method for forming a stretchable impedance sensor for use in electric cell-substrate impedance spectroscopy (ECIS), the method comprising steps of:
    disposing a layer of an uncured elastomer precursor between a pre-tensioned stretchable membrane in g tensioned state and a patterned conductive electrode on a rigid support such that the patterned conductive electrode is partially embedded within the uncured elastomer precursor along a bottom surface and side surfaces of the patterned conductive electrode, wherein the tensioned state stretched the pre-tensioned stretchable membrane by at least 4%;
    curing the layer of uncured elastomer precursor to produce a first layer of elastomeric material, the curing occurring while the pre-tensioned stretchable membrane is in the tensioned state;
    separating the rigid support from the patterned conductive electrode such that the patterned conductive electrode remains embedded within the first layer of elastomeric material;
    releasing the tensioned state on the pre-tensioned stretchable membrane to produce a released stretchable membrane;
    forming a second layer of the elastomeric material on the first layer of elastomeric material and the patterned conductive electrode such that the patterned conductive electrode is covered by the second layer, and thereafter removing a portion of the second layer of the elastomeric material to expose at least a portion of the patterned conductive electrode.

11. The method as recited in claim 10, wherein the removing uses masking to selectively expose the portion of the patterned conductive electrode.

12. The method as recited in claim 10, wherein the second layer has a thickness between 1 micron and 6 microns.

* * * * *

UNITED STATES PATENT AND TRADEMARK OFFICE
CERTIFICATE OF CORRECTION

PATENT NO.         : 10,393,685 B2
APPLICATION NO.    : 15/241686
DATED              : August 27, 2019
INVENTOR(S)        : Voiculescu et al.

Page 1 of 1

It is certified that error appears in the above-identified patent and that said Letters Patent is hereby corrected as shown below:

In the Claims

In Column 8; at Line 19 (which is Line 5 of Claim 10) reading "membrane in g" should read --membrane in a--

Signed and Sealed this
First Day of October, 2019

Andrei Iancu
*Director of the United States Patent and Trademark Office*